(12) United States Patent
Sutton et al.

(10) Patent No.: US 7,071,147 B2
(45) Date of Patent: Jul. 4, 2006

(54) WEED CONTROL PROCESS

(75) Inventors: Peter Bernard Sutton, Bracknell (GB); Rex Alan Witchert, Greensboro, NC (US)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/483,582

(22) PCT Filed: Jul. 8, 2002

(86) PCT No.: PCT/GB02/03119

§ 371 (c)(1),
(2), (4) Date: Jan. 9, 2004

(87) PCT Pub. No.: WO03/005820

PCT Pub. Date: Jan. 23, 2003

(65) Prior Publication Data

US 2004/0204319 A1     Oct. 14, 2004

(30) Foreign Application Priority Data

Jul. 11, 2001    (GB) .................................. 0116956.4

(51) Int. Cl.
*A01N 43/70*     (2006.01)
*A01N 43/707*     (2006.01)
*A01N 33/22*     (2006.01)
*A01P 13/00*     (2006.01)

(52) U.S. Cl. ...................... 504/133; 504/229; 504/234; 504/348; 504/350

(58) Field of Classification Search ................ 504/133, 504/229, 234, 348, 350
See application file for complete search history.

(56) References Cited

U.S. PATENT DOCUMENTS 4,937,386 A *   6/1990   Ueda et al. .................. 504/348
5,698,493 A     12/1997   Purnell et al.
6,046,134 A *   4/2000   De Gennaro et al. ....... 504/133

FOREIGN PATENT DOCUMENTS

EP    0 186 118    *   7/1986

OTHER PUBLICATIONS

Penn State College of Agricultural Sciences; "Callisto Herbicide Receives Federal Registration"; Penn State Weed Management, 2001.

* cited by examiner

*Primary Examiner*—S. Mark Clardy
(74) *Attorney, Agent, or Firm*—Rebecca Gegick

(57) ABSTRACT

A process of controlling triazine-tolerant weeds by the application of a combination of mesotrione and a triazine to the locus of said weeds is disclosed.

10 Claims, No Drawings

WEED CONTROL PROCESS

This application is a 371 filing of International Application No. PCT/GB02/03119, filed Jul. 8, 2002, the contents of which are incorporated herein by reference.

This invention relates to the use of a combination of mesotrione and a herbicidal triazine to control the growth of undesired target plants that show triazine tolerance.

The protection of crops from weeds and other vegetation that inhibits crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Commercial herbicides and some that are still in development are described in The Pesticide Manual, 12th edition, published in 2000 by the British Crop Protection Council. All the herbicides specifically named in this application can be found in The Pesticide Manual.

Triazines are one known class of herbicides. In normal use, these have proved to be very effective across a wide range of weeds. However, an increasing problem encountered in agriculture is the appearance of weeds that have developed a tolerance to triazines. By 'tolerance' is meant that these weeds are less easily damaged or killed by the application of triazine than the normal phenotype. Typically, these weeds show little or no damage when triazines are applied at normal application rates. This tolerance arises naturally and occurs because of the selection pressure exerted on the weed population by repeated application of triazine herbicides. Some weeds have developed almost complete tolerance to triazines, that is, they are virtually undamaged by triazines at the normal commercial application rates. Sometimes the word 'resistant' is also used to describe such weeds, in particular where they have the inherited ability to survive treatment by a triazine.

Triazine tolerance is obviously a problem, because either the weeds thrive to an increasing degree, which can drive down crop yields, or alternatively increased quantities of triazine must be used, which increases cost and risks environmental damage.

We have now discovered that a mixture of mesotrione and triazines can be used to control triazine-tolerant weeds. Mesotrione is a known herbicide. Mixtures of mesotrione and atrazine (a triazine) are known to have a synergistic effect in killing certain weeds and this is disclosed in U.S. Pat. No. 5,698,493.

However, one would not expect this mixture to have any effect, over and above the effect of the mesotrione, when applied over triazine-tolerant weeds, since, by definition, triazines have little or no effect on these at normal application rates. Contrary to this expectation, we have surprisingly found that the presence of mesotrione appears to restore the tolerant weeds' susceptibility to triazines, in some cases making them almost as susceptible to triazine as the normal non-tolerant weeds.

According to the present invention there is provided a process of controlling triazine-tolerant weeds by the application of a combination of mesotrione and a triazine to the locus of said weeds.

The combination can be applied sequentially, with either component being applied first, although preferably the mesotrione is applied first. Preferably the components are applied within 3 days and most preferably 24 hours of each other. Alternatively and preferably, the mesotrione and the triazine are applied together as a single composition.

In the field, preferably, the mesotrione is applied at a rate of at least 20 g a.i/ha, more preferably at least 50 g a.i/ha. Preferably the mesotrione is applied at less than 210 g/ha, more preferably less than 150 g/ha. Preferably the triazine is applied at a rate of at least 0.1 kg/ha more preferably at least 0.5 kg/ha Preferably the triazine is applied at less than 2 kg/ha, more preferably less than 1 kg/ha. In glasshouse tests, much lower levels of both components can be used. For example, in glasshouse tests, the mesotrione is preferably applied at a rate of 0.1 to 10 g/ha, more preferably 0.3 to 5 g/ha, most preferably 0.5 to 4 g/ha, and preferably the triazine is applied at a rate of 1 to 100 g/ha, more preferably 5 to 80 g/ha, most preferably 15 to 60 g/ha.

The mesotrione can be in the form of a metal salt, for example a copper salt as disclosed in U.S. Pat. No. 5,912,207.

Examples of triazines are ametryne, atrazine, cyanazine, desmetryne, dimethametryne, prometon, prometryne, propazine, terbumeton, terbuthylazine, terbutryne, trietazine, simazine and simetryne. As used herein, 'triazine' also includes triazinones, such as metribuzin. Atrazine, metribuzin and terbuthylazine are preferred, particularly atrazine.

The process of the invention involves applying the compositions by a convenient method to the locus of the tolerant weeds where control is desired. The "locus" is intended to include soil, seeds, and seedlings, as well as established vegetation.

The process can be used in areas where there are no desired plants, such as crops, or where desired plants, such as crops, have been planted, but have not yet emerged ('preemergence'). The process can also be used over a wide range of growing desired plants, such as crops (postemergence). Examples of crops are corn (maize), wheat, rice, potato or sugarbeet. Suitable desired plants include those which are tolerant to one or more of mesotrione and the triazine, particularly when the process is used postemergence, or tolerant to any other herbicide, such as glyphosate that can be additionally included in the combination. The tolerance can be natural tolerance which is inherent or which is produced by selective breeding or can be artificially introduced by genetic modification of the desired plants. Tolerance means a low susceptibility to damage caused by a particular herbicide. Plants can be modified or bred so as to be tolerant, for example to HPPD inhibitors like mesotrione, or EPSPS inhibitors like glyphosate. Corn (maize) is inherently tolerant to mesotrione and so the process is particularly useful for controlling triazine-resistant weeds in corn.

Examples of weeds with tolerant phenotypes include Redroot pigweed (AMARE), common lambsquarters (CHEAL) and black nightshade (SOLNI). The process is particularly effective over AMARE. Tolerant phenotypes are well know in the art and are easily identified by applying a triazine herbicide, such as atrazine, terbuthylazine or simazine and comparing the effect with application to a non-tolerant phenotype, also well known in the art, at a similar stage of growth.

The combination employed in the practice of the present invention can be applied in a variety of ways known to those skilled in the art, at various concentrations. The combination is useful in controlling the growth of undesirable vegetation by preemergence or postemergence application to the locus where control is desired.

The components of the combination according to the present invention (whether administered sequentially or together) are suitable applied as an agriculturally acceptable composition. The composition(s) preferably also comprise an agriculturally acceptable carrier therefor. In practice, the composition is applied as a formulation containing the various adjuvants and carriers known to or used in the industry for facilitating dispersion. The choice of formulation and mode of application for any given compound may affect its activity, and selection will be made accordingly. The compositions of the invention may thus be formulated as granules, as wettable powders, as emulsifiable concentrates, as powders or dusts, as flowables, as solutions, as suspensions or emulsions, or as controlled release forms such as microcapsules. These formulations may contain as little as about 0.5% to as much as about 95% or more by weight of active ingredient. The optimum amount for any given compound will depend upon formulation, application equipment, and nature of the plants to be controlled.

Wettable powders are in the form of finely divided particles that disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids that act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents, when used, normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as disking, dragging or mixing operations.

If necessary or desired for a particular application or crop, the composition of the present invention may contain an antidotally effective amount of an antidote (sometimes also called a 'safener') for mesotrione and/or triazine. Those skilled in the art will be familiar with suitable antidotes.

Further, other biocidally active ingredients or compositions may be combined with the synergistic herbicidal composition of this invention. For example, the compositions may contain, in addition to mesotrione and triazine, insecticides, fungicides, bactericides, acaracides or nematicides, in order to broaden the spectrum of activity.

As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of individual and combined herbicides, the application rate of any antidote, and the ratio of the individual herbicides to one another and/or to an antidote, as well as the nature of crops or weeds being tested, can affect the results of the test. Results may vary from crop to crop within the crop varieties.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined by the appended claims.

EXAMPLES

Sample weed plots were prepared by growing sample pots of a weed, Redroot pigweed (AMARE), both the normal wild variety, and, separately, a variant known to exhibit triazine tolerance. The soil was a silty clay loam mixed with fertiliser (12-12-12) at the rate of 128 g fertiliser to 10 gallons of soil.

The tolerant seeds were planted 13 days earlier than the non-tolerant seeds in order to get the seedlings to a similar size by the time the herbicide was applied. The time difference in planting was based on earlier observations of germination speed. On application of the herbicides, the tolerant plants had reached the 6-9 leaf stage, and the non-tolerant plants the 5-leaf stage.

Herbicide solutions were made by dissolving the herbicide(s) in tap water containing 0.5% of a commercial surfactant, 'Tween 20'. The solutions were applied at 200l/ha and 40 p.s.i pressure, using an 80015E nozzle. After spraying, the plants were placed in a glasshouse at 29/20° C. day/night temperature and 45/65% day/night relative humidity and a photoperiod of 14 hours.

The herbicides were applied as shown in Table 1. The figures in the mesotrione and atrazine columns are g/ha of herbicide applied to the test pots. The figures in the subsequent columns are percentage damage observed 13 days after application of the relevant herbicide composition. The numbers range from 0 (no effect) to 100 (dead plants). The main area of focus for the present invention is the effect on tolerant plants, and the effect on non-tolerant plants was only measured for comparative purposes.

From Table 1 it can be seen;

As expected, mesotrione causes damage to both tolerant and non-tolerant plants (compositions C1 to C3).

As expected, Atrazine alone had no effect at all on the tolerant plants (Compositions C4 to C7), while significantly damaging the non-tolerant plants.

Surprisingly, adding atrazine and mesotrione together causes damage that is significantly in excess of that caused by the mesotrione alone. For example, Composition 8 would be expected to give a damage level of 2 on tolerant plants, since the 0.90 g/ha of mesotrione gives a damage level of 2 and the 60 g/ha atrazine has no effect (Composition C7). However, Composition 8 actually gives a damage level of 46. At higher levels of mesotrione (Compositions 9 to 12), the damage levels on tolerant plants approach those on non-tolerant plants. This ability to circumvent the weeds' triazine resistance by the addition of mesotrione is an important breakthrough.

TABLE 1

| | Mesotrione g/ha | Atrazine g/ha | Non-Tolerant Observed | Tolerant Observed | Expected |
|---|---|---|---|---|---|
| C1 | 0.30 | — | 2 | 0 | — |
| C2 | 0.90 | — | 7 | 2 | — |
| C3 | 2.70 | — | 38 | 29 | — |
| C4 | — | 5 | 3 | 0 | — |
| C5 | — | 15 | 18 | 0 | — |
| C6 | — | 30 | 37 | 0 | — |
| C7 | — | 60 | 60 | 0 | — |
| 1 | 0.30 | 5 | 30 | 2 | 0 |
| 2 | 0.30 | 15 | 59 | 1 | 0 |
| 3 | 0.30 | 30 | 64 | 4 | 0 |
| 4 | 0.30 | 60 | 84 | 11 | 0 |
| 5 | 0.90 | 5 | 62 | 7 | 2 |
| 6 | 0.90 | 15 | 87 | 13 | 2 |
| 7 | 0.90 | 30 | 91 | 46 | 2 |
| 8 | 0.90 | 60 | 97 | 46 | 2 |
| 9 | 2.70 | 5 | 86 | 75 | 29 |
| 10 | 2.70 | 15 | 93 | 81 | 29 |
| 11 | 2.70 | 30 | 97 | 80 | 29 |
| 12 | 2.70 | 60 | 99 | 89 | 29 |

The invention claimed is:

1. A process of controlling triazine-tolerant weeds by the application of a combination of mesotrione and a triazine herbicide to the locus of said weeds.

2. A process according to claim 1, wherein the mesotrione and triazine are applied sequentially.

3. A process according to claim 2, wherein the mesotrione is applied first.

4. A process according to claim 1, wherein the mesotrione and triazine are applied together.

5. A process according to claim 4, wherein the mesotrione and triazine are applied together as a single composition.

6. A process according to claim 1, wherein the triazine is selected from the group consisting of ametryne, atrazine, cyanazine, desmetryne, dimethametryne, prometon, prometryne, propazine, terbumeton, terbuthylazine, terbutryne, trietazine, simazine, simetryne and metribuzin.

7. A process according to claim 6, wherein the triazine is selected from the group consisting of atrazine, metribuzin and terbuthylazine.

8. A process according to claim 7, wherein the triazine is atrazine.

9. A process according to claim 1, wherein the mesotrione is applied at a rate of 20 to 210 g/ha.

10. A process according to claim 9, wherein the triazine is applied at a rate of 0.1 to 2 kg/ha.

* * * * *